United States Patent [19]

Ashmead

[11] Patent Number: 4,830,716
[45] Date of Patent: * May 16, 1989

[54] PREPARATION OF PHARMACEUTICAL GRADE AMINO ACID CHELATES

[75] Inventor: Harvey H. Ashmead, Kaysville, Utah

[73] Assignee: Albion International, Inc., Clearfield, Utah

[*] Notice: The portion of the term of this patent subsequent to Jul. 8, 2003 has been disclaimed.

[21] Appl. No.: 882,150

[22] Filed: Jul. 3, 1986

[51] Int. Cl.$^4$ ................................................ C25D 1/02
[52] U.S. Cl. .............................. 204/72; 204/59 QM; 556/50; 556/134; 556/148
[58] Field of Search .................... 556/50, 148, 134; 204/59 QM, 72

[56] References Cited

U.S. PATENT DOCUMENTS

| | | | |
|---|---|---|---|
| 4,172,072 | 10/1979 | Ashmead | 556/148 X |
| 4,216,143 | 8/1980 | Ashmead | 556/50 X |
| 4,216,144 | 8/1980 | Ashmead | 556/148 X |
| 4,448,716 | 5/1984 | Tsau | 556/148 X |
| 4,599,152 | 7/1986 | Ashmead | 204/72 |

*Primary Examiner*—Paul F. Shaver
*Attorney, Agent, or Firm*—Thorpe, North & Western

[57] ABSTRACT

Pharmaceutical grade amino acid chelates, free of interfering anions, are made by reacting an amino acid ligand with a metal member selected from the group consisting of elemental metals, metal oxides, metal hydroxides and metal carbonates in an aqueous environment wherein the ligand to metal mole ratio is at least 2:1 and recovering the amino acid chelate from said aqueous environment by means of spray or drum drying. The reaction may be carried out in the presence of non-interfering anions such as anions from citric acid, ascorbic acid, acetic acid, carbonic acid and ammonium and alkali metal salts thereof.

25 Claims, No Drawings

PREPARATION OF PHARMACEUTICAL GRADE AMINO ACID CHELATES

BACKGROUND OF THE INVENTION

This application relates to methods of preparing amino acid chelates which are essentially free of contaminating anions. More particularly, this invention relates to methods of preparing pharmaceutical grade amino acid chelates. This application is related to copending application Ser. No. 738,065 filed May 24, 1985 entitled "Pure Amino Acid Chelates", which will issue July 8, 1986 as U.S. Pat. No. 4,599,152.

Amino acid chelates are products resulting from the reaction of a polypeptide, dipeptide or naturally occurring alpha amino acids with a metal ion having a valence of two or more to form a ring structure wherein the positive electrical charges of the metal ion are neutralized by the electrons available through the carboxylate or free amino groups of the alpha amino acid. For convenience sake, metal ions having a valence of two or more will simply be referred to as divalent metal ions or divalent cations.

Chelate formation through neutralization of the positive charges of the divalent metal ions can be through the formation of ionic, covalent or coordinate covalent bonding. In the past, amino acid chelates have generally been made by first dissolving a water soluble divalent metal salt in water. An amino acid ligand is then reacted with the metal ion at a ratio of ligand to metal of at least 1:1 and preferably at least 2:1. Often, the ligand is a hydrolysis product obtained by acid, base, base-acid, or base-acid-base hydrolysis. In such cases, the by products from hydrolysis, such as anions including chlorides, sulfates, phosphates and nitrates, and cations, including potassium and sodium remain in the hydrolysate. Reaction products of metal salts with proteins or with acid and/or base hydrolyzed proteins are taught in U.S. Pat. Nos. 2,960,406 (Cardon); 3,396,104 (Miller); 3,463,858 (Anderson); 3,775,132 (Richards); 4,020,158 (Ashmead et al); 4,103,003 (Ashmead) and 4,172,072 (Ashmead). In order for the reaction to proceed to completion with the formation of a cyclic chelate ring, the amino acid has had to be at a pH which is preferably above, or more basic than, the isoelectric point of the amino acid. For that reason, a certain amount of an alkali metal hydroxide, carbonate or bicarbonate has usually been added to the reaction mixture.

Most water soluble salts used in making amino acid chelates have been either sulfates or chlorides. Using the sulfate ion as exemplary, the reaction has generally proceeded as follows:

$$2NaOH + MSO_4 + 2NH_2CHCOOH \longrightarrow$$
$$\phantom{2NaOH + MSO_4 + 2NH_2CH} | $$
$$\phantom{2NaOH + MSO_4 + 2NH_2CHCOO} R$$

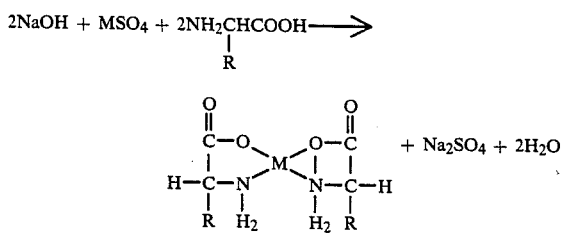

$+ Na_2SO_4 + 2H_2O$ where M is a bivalent metal cation and R is a radical of a naturally occurring amino acid, dipeptide or polypeptide. It is apparent from the above formula that the sulfate anion is present in the reaction mixture in the form of sodium sulfate. U.S. Pat. No. 2,877,253 teaches a product formed by the reaction of one mole of glycine with one mole of ferrous sulfate. That patent indicates that the sulfate anion becomes tied up in the reaction which allegedly forms a ferrous sulfate-glycine complex. Whether or not the sulfate actually participates in the reaction, or is present as the salt of an alkali metal, it nevertheless is present in the reaction mixture. Such products are difficult, if not impossible, to purify. While sodium sulfate, per se, is water soluble, the reaction between a metal sulfate and an amino acid is never carried to 100% completion and the sulfate ion is always present. The same holds true for the presence of chloride ions when utilizing a metal chloride salt for amino acid chelate preparation.

Even if one were to attempt to wash out the excess sulfate or chloride ions with repeated washes, such an attempt could well be counter productive inasmuch as glycine and other amino acid ligands are also soluble to a degree. Hence, depending upon pH, the unreacted ligands or weakly held ligands could also be removed along with the unwanted anions.

Other methods teaching the reaction of metal salts with ligands made up of protein, protein hydrolysates or amino acids are found in U.S. Pat. Nos. 3,168,541 (Hobbs); 3,969,540 (Jensen); 4,167,564 (Jensen); 4,216,143 (Ashmead) and 4,216,144 (Ashmead).

These salt by-products in amino acid chelates cause a variety of problems, not the least of which is cost. When salts are present, it is impossible to obtain an amino acid chelate with as high a metal content as with the salts absent. It also costs both to prepare and ship the unneeded salt. Moreover, these salts often pick up moisture and make handling of the product difficult. Most importantly, the health of humans, plants and animals receiving amino acid chelates is, in general, affected adversely by the presence of these salts.

In U.S. Pat. No. 4,599,152 (Ashmead), electrolytic methods for preparing anion free amino acid chelates are taught. While these methods are successful in preparing such pure forms of chelates, they are relatively expensive and time consuming.

OBJECTS AND SUMMARY OF THE INVENTION

It is an object of the present invention to provide methods for the preparation of substantially pure amino acid chelates suitable for pharmaceutical use.

It is also an object of this invention to provide methods of preparing amino acid chelates which are substantially free of interfering anions.

Another object of this invention is to provide methods of preparing pharmaceutical grade amino acid chelates on a commercial scale.

These and other objects may be obtained by means of one or more chemical methods wherein one or more amino acid, dipeptide, polypeptide or protein hydrolysate ligands, free of unwanted anionic impurities, are reacted with a metal ion in an environment wherein the by-products of the reaction are water, hydrogen, or water and carbon dioxide. Suitably, pure elemental metals, metal oxides, metal hydroxides and metal carbonates are reacted with purified amino acids, dipeptides, polypeptides or protein hydrolysates in an aqueous environment under appropriate conditions to cause the interaction between the metal and amino acids to form an amino acid chelate.

DETAILED DESCRIPTION OF THE INVENTION

There follows a detailed description of four embodiments of the invention. The basic principle of each method is to have the reactants produce the desired amino acid chelate and a substance such as water, carbon dioxide or hydrogen which can be easily removed from the chelate thus formed. The common feature in each method is also the key to its successful operation. That key is that amino acids function as acids. While that statement may not sound so profound, many researchers in the past have not considered amino acids, including dipeptides or polypeptides, to be sufficiently acid to be a propelling force for a reaction. Even though amino acids are very weak (pKa for glycine—9.6), their acidity is great enough to cause the desired reactions to occur. In each case, the acidic amino acid proton is removed to form water or hydrogen and the nitrogen lone pair on the alpha amino acid nitrogen atom becomes available, along with the carboxylate ion, for bonding with the chosen metal. The metal will preferably be a member selected from the group consisting of calcium, magnesium, manganese, iron, copper, and zinc. However, other bioessential divalent metal ions such as chromium, selenium, cobalt, molybdenum and vanadium could also be utilized.

Each embodiment to be described in detail is illustrated by the following general equations:

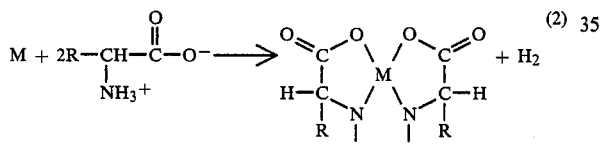

(2)

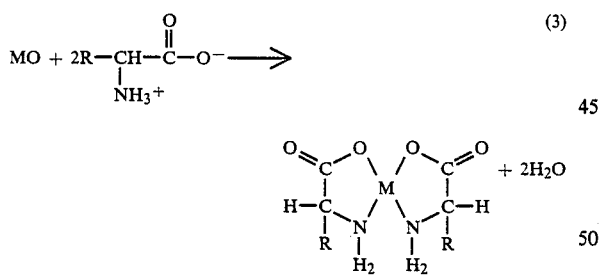

(3)

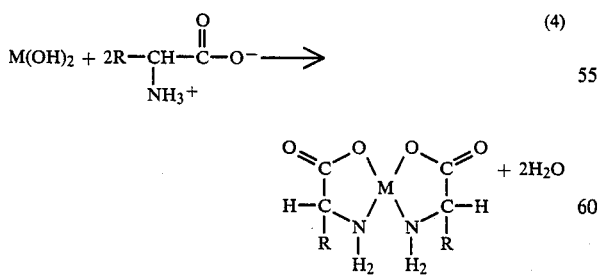

(4)

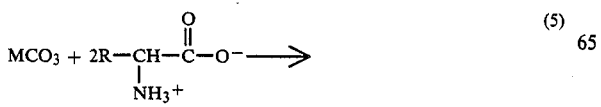

(5)

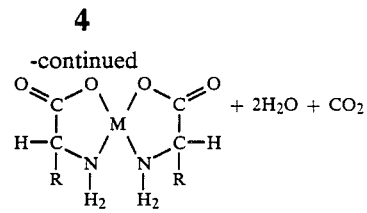

$+ 2H_2O + CO_2$ wherein M is a divalent metal cation and R is a radical of a naturally occurring amino acid, or dipeptide, tripeptide or quadrapeptide moiety.

The amino acid chelates formed from the methods of this invention will ordinarily contain between two to four ligands for each divalent metal ion regardless of the oxidation state or valence of the metal ion. The following structural formulae, in addition to those shown above in equations (1)–(5), are representative of the amino acid chelates which may be prepared by the methods of this invention:

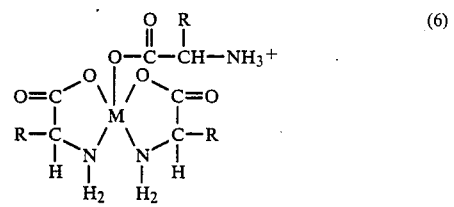

(6)

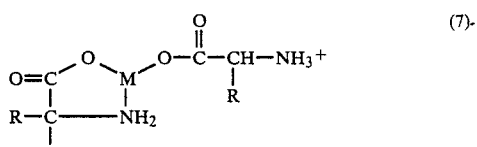

(7)

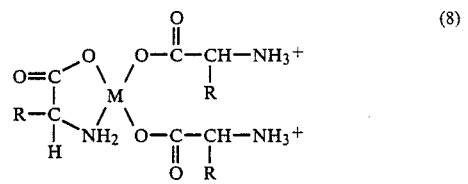

(8)

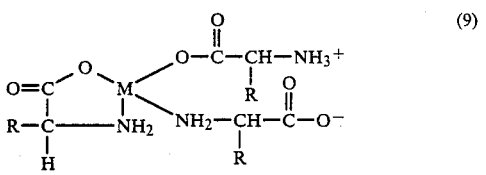

(9)

wherein M and R have the same meanings previously given. It will be noted in each of these formulae that the metal atom is completely neutralized and is carrying no net electrical charge. Again, it is to be stressed that these formulae are but representative and that other structures formed by the combination of a divalent metal ion with at least two amino acid ligands are also within the scope of the present invention. The upper limit of amino acid ligands to metal ion is determined only by the capacity of the divalent metal ion to interact with the particular ligands used. Therefore, while ligand to metal ratios of 2:1 to 4:1 are preferred, chelates having a ligand to metal ratio in excess of 4:1 are also considered to be part of this invention. It is taught in U.S. Pat. No. 4,167,564 that ligand to metal ratios can go as high as 16:1. Products having a ligand to metal ratio of 1:1 are usually in the form of complexes or salts and are not chelates. Also, they are generally impure due to the fact that the valence requirements of the metal ion are not satisfied by the presence of a single ligand. However, to the extent that 1:1 complexes of ligand to metal are acceptable for end use, they can be prepared by the methods disclosed herein with minimum impurities.

While any suitable amino acid or protein hydrolysate ligand may be utilized as long as it is free of interfering anions, it has been found most productive to utilize low molecular weight ligands such that the chelate, when formed, will have a molecular weight not in excess of 1500. Preferably, the molecular weights will not exceed 1000 and most preferably not be in excess of 500. Chelates having molecular weights of 300 and under are especially preferred as they are absorbed into biological tissues much more rapidly. These chelates, when orally ingested, are believed to be absorbed into humans and animals via a dipeptide absorption pathway. The intact absorption of dipeptide like amino acid chelates is documented in the book "Intestinal Absorption of Metal Ions and Chelates", by Ashmead, et al, published by Charles C. Thomas, Springfield, Ill., 1985.

Since the desired molecular weight of the amino acid chelates is limited, relative to the molecular weight of proteins, it is preferable to utilize as the amino acid source, purified amino acids selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine or dipeptides, tripeptides or quadrapeptides formed by any combinations of the above.

The metals are preferably selected from the group consisting of calcium, magnesium, manganses, iron, copper and zinc. Other bioessential metal ions such as cobalt, chromium, molybdenum, vanadium or selenium may also be utilized.

It is anticipated that it will generally be desirable to produce pharmaceutical grade metal chelates in which the metal is the same throughout the product. However, there may be instances when a mixture of metal chelates may be desired in which the chelates have amino acid ligands combined with two or more differing metals. Such mixtures can be produced by mixing of finished products or, if feasible, by utilizing a mixture of metal ions in the reaction with the amino acid ligands.

The amino acid chelates prepared according to this invention are of a quality suitable for pharmaceutical use and are considered to be substantially pure. By pure or pharmaceutical grade is meant that they are free of the interfering metal salt anions referred to above, i.e. sulfates, nitrates, chlorides, etc. However, in the formation of these pure chelates, it is sometimes preferable to utilize weak organic acids or their alkali metal or ammonium salts. In addition, buffering agents may also be used. Typical of these are citrates, ascorbates, acetates, carbonates and bicarbonates. These reagents are soluble and may be removed from the precipitated amino acid chelates by washing, if desired. In certain instances, an electrical current may be utilized to provide the potential necessary to complete certain reactions. In such instances, a certain amount of hydronium or hydroxyl ions may be formed. These ions do not affect the purity of the chelates and recombine to form water.

The term "interfering anion" is utilized throughout this disclosure to refer to the aforementioned sulfates, nitrates, chlorides, etc. These anions not only have the disadvantages already mentioned, they are also believed to interfere with metal ion absorption in biological systems. For example, the sulfate ion is believed to interfere with the absorption of amino acid chelates through the intestinal walls of humans and animals. Thus, it is apparent that there are multiple reasons for not wanting these anions present. On the other hand, anions such as citrates, ascorbates, bicarbonates and the like are not "interfering" and in fact may be beneficial. In the gastrointestinal tract, they may act as buffering agents protecting the amino acid chelates from destruction by the acidic media of the stomach thereby allowing them to pass into the small intestine intact where they are absorbed. Thus, for purposes of this disclosure, whenever the term "anion free", "pharmaceutical grade", "pure" or "substantially pure" or the equivalent are utilized in describing the amino acid chelates prepared by the processes of this invention, it is intended to mean free of anions of inorganic acids but is not meant to exclude added amounts of non-interferring anions of weak organic acids, hydroxyl ions or buffering agents.

Elemental Metal Method

Active metals such as calcium, magnesium and manganese, when placed in the presence of amino acids, reduce the acidic amino acid proton to hydrogen which is given off as hydrogen gas. Iron, zinc and copper are not sufficiently reactive to cause this reduction to occur without the application of a slight potential to the metal. This may be done by the addition of electrolytes to an aqueous solution or by the application of an electric potential.

These reactions all occur in an aqueous medium wherein the amino acid ligand has been at least partially dissolved. The most obvious evidence for the reaction of metals with amino acids, using glycine for purposes of illustration, is the disappearance of the metal and the ebullition of hydrogen according to the reactions:

  (10)

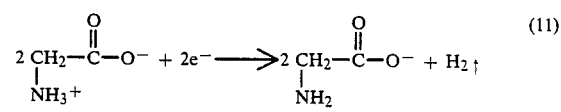  (11)

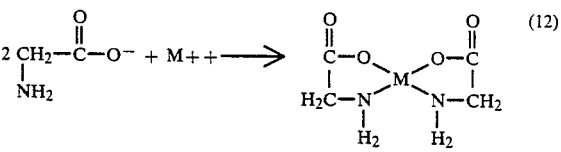  (12)

The pH of a glycine solution before reaction is about 6.0. When using calcium as the metal, the pH of the solution after the reaction, increases to about 9.4. With magnesium, the pH increases to about 10.5 and with manganese to about 9.0. A smaller pH increase, to about 7.8 is noted with iron. With zinc the pH increases to about 8.0 and with copper to about 7.5.

When using copper, it is necessary to apply a potential electrically. Other metals may also be ionized, or oxidized, using the metal as an anode in an electrolytic cell. The cathode can be any inert material such as graphite. The reaction proceeds according to equations (10), (11) and (12) above. In the completed reaction, the metal is oxidized as the protons on the amino acids are reduced. Whether using an electrolytic method or not, a weak electrolyte such as citric or ascorbic acid may be added to the aqueous solution to promote the reaction.

Eletrolytic methods using iron, copper, zinc and manganese as the metal and glycine as the amino acid source, have successfully qualitatively demonstrated the preparation of the corresponding amino acid chelate having a ligand to metal ratio of at least 2:1. In each instance, about 3 grams of glycine were admixed with 100 ml of water containing a small amount of citric acid. A small power supply producing 3 volts of D.C. was attached to the electrodes. When the surface area of the electrode was 20 cm$^2$, a current of 5 amps was observed to pass through the system.

The reaction is brought about by admixing the amino acid ligand in water, with or without an electrolyte, adding pure metal particles (or using a pure metal eletrode) and allowing the reaction to proceed under ambient conditions. The amount of amino acid added to the solution will be sufficient to provide a ligand to metal mole ratio of at least 2:0.

The following examples illustrate this preparative method.

EXAMPLE I

To 83 parts by weight of water was added 2 parts by weight of citric acid as a buffer-electrolyte. Glycine, 13 parts by weight, was added to the water and stirred until it had gone into solution. To this mixture was added 2 parts by weight of freshly prepared magnesium turnings. The reaction mixture was allowed to stand for 48 hours. Upon observation, the ebullition of hydrogen gas was noted. The pH of the solution gradually went from about 6.0 to 10.5 over the reaction period.

About 8 parts by weight of citric acid was added to the reaction mixture which was heated to about 100° C. to clarify it. This reaction mixture was then spray dried to provide a magnesium diglycine amino acid chelate powder having a magnesium content of about 10% w. and a glycine to magnesium ratio of about 2:1. When reconstituted in water, the pH of the resulting solution was about 8.0. The pH difference between the solution at the end of the reaction and the reconstituted solution is due to the minor amount of citric acid added to clarify the solution.

EXAMPLE II

The procedure of Example I was repeated using 1095 parts by weight water, 3.5 parts by weight each of citric acid and elemental manganese metal and 205 parts by weight glycine. The reaction was allowed to proceed over a 48 hours period and was then filtered to remove undissolved materials and spray dried to recover a manganese diglycine amino acid chelate having a manganese content of about 16% w. and having a melting point of about 203° C. The mole ratio of glycine to manganese was about 3:1. When reconstituted as an aqueous solution, the pH is about 7.0.

EXAMPLE III

To 87 parts by weight deionized water was added 9 parts by weight glycine and 2 parts by weight fructose. To this solution was very slowly added 2 parts by weight pure calcium metal with no mixing. The evolution of hydrogen gas was immediately accompanied by a rise in temperature of the solution to about 66° C. The heated solution was filtered and spray dried to produce a calcium diglycine amino acid chelate having a metal content of about 14% w. and a melting point of about 145° C. The mole ratio of glycine to calcium was about 2:1. When reconstituted in water the solution has a pH of about 9.6.

EXAMPLE IV

To about 700 mls of deionized water containing 50 gms citric acid was added 225 gms. glycine. A clear solution was formed. To this solution was slowly added 55.8 gms of elemental iron. The solution was heated at about 50° C. until all the iron was observed to go into solution (about 24 hours). The product was cooled, filtered and spray dried yielding an iron triglycine amino acid chelate.

Metal Oxide Method

Calcium, magnesium and zinc oxides react most readily with amino acids in aqueous solutions to form amino acid chelates. There is some evidence that other transition metals such as manganese, copper and iron also react to slowly form amino acid chelates. In the case of magnesium and calcium, the heat of reaction and change of pH indicate that the reaction has taken place. For example, in the case of magnesium, reacting with two moles of glycine, the pH of the glycine prior to magnesium oxide addition is about 6.0 and after the magnesium oxide is added the pH is raised to about 10.55 accompanied by the release of heat at about 6.5 kcal/mole.

The reaction between metal oxides and amino acids occurs because the metal oxides are basic and the amino acids are weak acids. When they react, water and the chelate are the only products produced. There are no interfering anions entering into the reaction as impurities. In the case of alkaline amino acids, such as arginine, it may be necessary to add a reaction aid, such as citric acid, to enable the reaction to proceed. The desired amount of ligand is preferably first at least partially dissolved in an aqueous solution along with any reaction aid, buffering or stabilizing agent. To this solution is then added the desired amount of the metal oxide and the solution is allowed to stand until the reaction is completed. Because metal oxides are relatively insoluble in water, relatively large amounts of water are required to get the metal oxide into solution and the reaction can proceed slowly. Therefore, sufficient amounts of water and time should be provided to allow the reaction to proceed to completion and at least until there is no more any evolution of heat. Upon completion, the solution is preferably filtered to remove any unreacted metal oxide before spray drying. Because large amounts of water are required in each of the embodiments of this invention, spray or drum drying is required to remove water and obtain the pharmaceutical grade amino acid chelate product.

EXAMPLE V

A solution was prepared consisting of 12.4 parts by weight of glycine dissolved in 82.2 parts by weight water containing 1.0 part by weight sodium carbonate. To this solution was added 4.4 parts by weight zinc oxide. The molar ratio of glycine to zinc was 3:1. The reaction mixture was allowed to stand for about 14 hours and turned an opalescent color. After standing, the mixture was heated to about 70° C. and spray dried to obtain a zinc triglycine amino acid chelate powder having a melting point of about 209° C. which turned red upon melting. The zinc content of the chelate was about 20% w. The dried product had a moisture content of about 7% w. and when reconstituted in water had a pH of about 8.0.

Metal Hydroxide Method

Almost all amino acid chelates can be prepared from the corresponding metal hydroxides; however, not all metal hydroxides are readily available or convenient to prepare. Calcium hydroxide can be prepared by the addition of calcium oxide to water, but hydroxides must be prepared from aqueous solutions containing metal salts, such as chlorides or nitrates, by being precipitated as metal hydroxides by the addition of sodium or potassium hydroxide. With magnesium, manganese and copper there is no problem in adding excess base. However, care must be taken with zinc and iron which react with excess hydroxide and are not effective in the production of chelates.

The driving force for the production of amino acid chelates from corresponding metal hydroxides is the production of the weak electrolyte, water, as shown in equation (4) above. The basicity of the metal hydroxides varies greatly with the stronger bases reacting more readily with the weakly acidic amino acids. The basicity and solubility of the principal metal hydroxides is $Ca > Mg > Mn > Fe > Zn > Cu$. This is better illustrated by the following table:

| Metal Hydroxide | Ksp | pH |
| --- | --- | --- |
| $Ca(OH)_2$ | $5.5 \times 10^{-6}$ | 12.35 |
| $Mg(OH)_2$ | $1.8 \times 10^{11}$ | 10.52 |
| $Mn(OH)_2$ | $1.9 \times 10^{-13}$ | 9.86 |
| $Fe(OH)_2$ | $8.0 \times 10^{-16}$ | 9.07 |
| $Zn(OH)_2$ | $1.2 \times 10^{-17}$ | 8.68 |
| $Cu(OH)_2$ | $2.2 \times 10^{-20}$ | 7.55 |

Because of the relative insolubility of metal hydroxides in water, sufficient water must be provided to bring the metal hydroxide into solution and it may be advantageous to allow a reaction mixture of metal hydroxides and amino acids to stand for a period of time to allow the reaction to proceed to completion.

EXAMPLE VI

Calcium oxide is added to water forming a saturated calcium hydroxide solution having an initial pH of about 12.75. Glycine is added to this solution in an amount to provide two moles of glycine per mole of calcium. There is a noticable evolution of heat and the pH decreases, to about 10.55 in a matter of a few minutes after adding glycine. It is calculated that the evolution of heat amounts to about 7 kcal/mole for the reaction of one mole of calcium hydroxide with two moles of glycine. The solution is filtered and the filtrate is spray dried to produce a calcium diglycine amino acid chelate having a calcium content of about 14% w.

In a different embodiment of this mode of preparation, it is not necessary to use excessive amounts of water. It has been found that a moist paste may be formed from a mixture of most metal hydroxides and amino acid ligands in the desired ratio. The paste is allowed to stand for a period of a few hours or even days. Again, there is a noticable evolution of heat and decreasein pH. The completed reaction is then diluted with water, filtered to remove unreacted insolubles and spray dried.

Metal Carbonate Method

Like their metal oxide and hydroxide counterparts, metal carbonates are relatively insoluble in aqueous solutions. Therefore, sufficient water must be utilized. However, even with small amounts of water there is generally sufficient solubility that an acid-base like reaction occurs between the metal carbonate and the amino acid ligands to cause the reaction to proceed according to equation (5) with the release of carbon dioxide and water. Therefore, the paste method described for the metal hydroxide embodiment is also applicable to the metal carbonate technique. The solubility of metal carbonates may be increased by the addition of carbon dioxide or a soluble carbonate, such as sodium carbonate, to the solution. Care must be taken not to lower the pH to the point that the reaction between the metal from the metal carbonate and amino acid does not take place. The following example illustrates this mode of preparation.

EXAMPLE VII

A copper carbonate solution was prepared by adding 6.1 parts by weight of cupric carbonate to 80.9 parts by weight water. The copper carbonate was rendered more soluble by the addition of 4.9 parts by weight sodium carbonate. This solution was allowed to stand without agitation for about two hours. To this solution was added 8.2 parts by weight of glycine and the mixture was slowly stirred for about two more hours. A hazy blue solution was observed. To this solution was added 65 parts by weight of a 15% citric acid solution and the mixture was stirred until a clear blue solution was observed. This solution was spray dried resulting in a copper diglycine amino acid powder having a copper content of about 14% w. and which melted at about 194° C. Upon being reconstituted in water, the pH of the resulting solution was about 7.5.

The above examples and descriptions of the various embodiments are sufficient to allow one skilled in the art to practice the invention with considerable latitude. Since virtually all chemical reactions are in equilibrium, it is desirable to choose those reaction conditions most suited to amino acid chelate preparation, i.e. which will drive the reaction to the right in the above equations. Thus, providing sufficient water to enable the metal, metal oxides, metal hydroxides or metal carbonates to come into solution as the reaction proceeds in the formation of the amino acid chelates is an important aspect. If insufficient water is present to allow all of the metal compound to come into solution at once, the reaction may proceed more slowly. As a metal ion is reacted with amino acid ligands to form a chelate, additional metal ions from the metal source will come into solution. Hence, in the case of a paste, it may take considerable time for the reaction to proceed to equilibrium. As previously mentioned, the use of considerable amounts of water is not a disadvantage in the present invention. Many spray or drum drying techniques require that the solids content of a mixture to be dried be under 30% w.

The suitability of any particular metal, metal oxide, metal hydroxide or metal carbonate and the oxidation state of the metal ion may be determined without undue experimentation. In some instances, the higher oxidation state of a transition metal such as copper is required since the ion must be in at least a divalent state. However, in the case of iron, either ferric or ferrous ions may prove acceptable and the same holds true for manganese. Hence, no attempt has been made to limit the metal ions to any particular oxidation state as long as they are at least divalent.

While glycine has been used in the above examples for purposes of illustration, the choice of the particular amino acid ligands may be tailored to the particular needs of a human, animal or plant. Certain amino acid chelates or combinations of amino acid chelates may be targeted to specific tissue sites as taught in copending patent application Ser. No. 826,786 filed Feb. 6, 1986.

The particular reaction aids, buffering agents, electrolytes and solubilizing agents have been described with sufficient clarity that one skilled in the art may recognize those which can be adapted to use in the present invention to produce a pharmaceutically acceptable amino acid chelate. Hence, the invention is not limited to the specific agents or materials taught in the disclosure but is considered to encompass all functional equivalents thereto and is limited only by the scope of the appended claims.

I claim:

1. A method for the preparation of pharmaceutical grade amino acid chelates, substantially free of interfering anions, which comprises reacting an anion free ligand selected from the group consisting of naturally occurring amino acids, or dipeptides, tripeptides or quadrapeptides thereof, in an aqueous environment, with a metal member selected from the group consisting of elemental metals, metal oxides, metal hydroxides and metal carbonates, wherein the metal is member selected from the group consisting of calcium, copper, iron, magnesium, manganese and zinc, and wherein the mole ratio of ligand to metal is at least 2:1 and recovering the amino acid chelate thus formed therefrom.

2. A method according to claim 1 wherein the molecular weight of the amino acid chelate formed does not exceed 1500 and wherein the mole ratio of ligand to metal is between about 2:1 to 4:1.

3. A method according to claim 2 wherein an electrical potential is applied to the aqueous environment to expedite the reaction.

4. A method according to claim 2 wherein an electrolyte is added to the aqueous environment to expedite the reaction.

5. A method according to claim 4 wherein the electrolyte is a member selected from the group consisting of citric acid, ascorbic acid, acetic acid, carbonic acid and ammonium and alkali metal salts thereof.

6. A method according to claim 3 wherein the potential is a direct electrical current and wherein the elemental metal forms the anode of an electrolytic cell.

7. A method according to claim 2 wherein the metal member is a metal oxide selected from the group consisting of calcium oxide, copper oxide, iron oxide, magnesium oxide, manganese oxide and zinc oxide.

8. A method according to claim 7 wherein the metal oxide is a member selected from the group consisting of calcium oxide, magnesium oxide and zinc oxide.

9. A method according to claim 7 wherein said aqueous environment consists of sufficient water to bring said metal oxide at least partially into solution.

10. A method according to claim 9 wherein said reaction is carried out in the presence of an agent selected from the group consisting of citric acid, ascorbic acid, acetic acid, carbonic acid and ammonium and alkali metal salts thereof.

11. A method according to claim 9 wherein said amino acid chelate is recovered from said aqueous environment by means of spray drying or drum drying.

12. A method according to claim 2 wherein the metal member is a metal hydroxide selected from the group consisting of calcium hydroxide, copper hydroxide, iron hydroxide, magnesium hydroxide, manganese hydroxide and zinc hydroxide.

13. A method according to claim 12 wherein said aqueous environment consists of sufficient water to bring said metal hydroxide at least partially into solution.

14. A method according to claim 13 wherein said reaction is carried out in the presence of an agent selected from the group consisting of citric acid, ascorbic acid, acetic acid, carbonic acid and ammonium and alkali metal salts thereof.

15. A method according to claim 13 wherein said amino acid chelate is recovered from said aqueous environment by means of spray drying or drum drying.

16. A method according to claim 12 wherein said aqueous environment consists of only sufficient water to form a moist paste of said metal hydroxide and amino acid chelate ligand.

17. A method according to claim 16 wherein said moist paste is allowed to stand under ambient conditions for a determined period of time after which it is diluted with water, filtered and the filtrate is spray dried or drum dried.

18. A method according to claim 2 wherein the metal member is a metal carbonate selected from the group consisting of calcium carbonate, copper carbonate, iron carbonate, magnesium carbonate, manganese carbonate and zinc carbonate.

19. A method according to claim 18, wherein said aqueous environment consists of sufficient water to bring said metal carbonate at least partially into solution.

20. A method according to claim 19 wherein said reaction is carried out in the presence of an agent selected from the group consisting of citric acid, ascorbic acid, acetic acid, carbonic acid and ammonium and alkali metal salts thereof.

21. A method according to claim 20 wherein said agent is a member selected from the group consisting of carbonic acid an ammonium and alkali metal salts thereof.

22. A method according to claim 21 wherein said metal carbonate is copper carbonate.

23. A method according to claim 19 wherein said amino acid chelate is recovered from said aqueous environment by means of spray drying or drum drying.

24. A method according to claim 18 wherein said aqueous environment consists of only sufficient water to form a moist paste of said metal carbonate and amino acid chelate ligand.

25. A method according to claim 24 wherein said moist paste is allowed to stand under ambient conditions for a determined period of time after which it is diluted with water, filtered and the filtrate is spray dried or drum dried.

* * * * *

UNITED STATES PATENT AND TRADEMARK OFFICE
CERTIFICATE OF CORRECTION

PATENT NO. : 4,830,716
DATED : May 16, 1989
INVENTOR(S) : Harvey H. Ashmead

It is certified that error appears in the above-identified patent and that said Letters Patent is hereby corrected as shown below:

<u>Title page,</u>
Item [*] Notice, change "The portion of the term of this patent subsequent to July 8, 2003 has been disclaimed." to -- This patent is subject to a terminal disclaimer. --

Signed and Sealed this

Third Day of August, 2004

JON W. DUDAS
*Acting Director of the United States Patent and Trademark Office*

US004830716B1

REEXAMINATION CERTIFICATE (3946th)

United States Patent [19]
Ashmead

[11] B1 4,830,716
[45] Certificate Issued Dec. 7, 1999

[54] PREPARATION OF PHARMACEUTICAL GRADE AMINO ACID CHELATES

[75] Inventor: Harvey H. Ashmead, Kaysville, Utah

[73] Assignee: Albion International, Inc., Clearfield, Utah

Reexamination Requests:
No. 90/004,203, Apr. 3, 1996
No. 90/004,799, Oct. 16, 1997

Reexamination Certificate for:
Patent No.: 4,830,716
Issued: May 16, 1989
Appl. No.: 06/882,150
Filed: Jul. 3, 1986

[51] Int. Cl.$^6$ .............................. C25B 3/12; C07F 13/00; C07F 15/00; C07F 1/08
[52] U.S. Cl. ............................ 205/457; 205/799; 556/50; 556/116; 556/134; 556/148
[58] Field of Search .............................. 556/50, 116, 134, 556/148; 205/457, 799

[56] References Cited

U.S. PATENT DOCUMENTS

| | | | | |
|---|---|---|---|---|
| 2,396,115 | 3/1946 | Nicholls | .................................. | 260/535 |
| 3,440,054 | 4/1969 | Sair | .............................................. | 99/14 |
| 3,969,540 | 7/1976 | Jensen | ...................................... | 426/657 |
| 4,172,072 | 10/1979 | Ashmead | ................................ | 260/115 |

OTHER PUBLICATIONS

R. G. Bineev, et al., "The Biological Activity of Cheleates of 3d–Elements With Methionine," Ozdorovitel'nye Meropriyatiya Prom. Zhivotnovod. Kompleksakh Infekts. Zabol., 71–6, 1983.

D. N. Sen, et al., "Infrared Absorption Spectra of Inorganic Coördination Complexes. I. The Nature of Chelation Bonding in Bis(glycino)–copper(II) Monohydrate and Bis–(glycino)–nickel(II) Dihydrate," Journal of the American Chemical Society, vol. 77, pp. 211–12, Jan. 5, 1955.

A. J. Stosick, "The X–Ray Investigation of Copper dl–α–Aminobutyrate," J. Am. Chem. Soc., vol. 67, pp. 362–365, Mar., 1945.

P. A. Kober and K. Sugiura, "The Copper Complexes of Amino Acids, Peptides and Peptones," The Journal of Biological Chemistry, vol. 13, No. 1, pp. 1–13, 1912.

P.A. Kober and K. Sugiura, "The Copper Complexes of Amino Acids, Peptides and Peptones," American Chemical Journal, vol. 48, No. 5, pp. 383–411, Nov. 1912.

Advances In Protein Chemistry, edited by C. B. Anfinsen, Jr., M. L. Anson, J. T. Edsall, and F. M. Richards, vol. 22, Academic Press, New York, pp. 269–270, 391, 1967.

A. M. Mathieson and H. K. Welsh, "The Crystal Structure of Copper Proline Dihydrate," Acta Cryst., vol. 5, pp. 599–604, 1952.

D. Van Der Helm and W. A. Franks, "The Crystal Structure of Bis(L–serinato)copper(II)," Acta Cryst., vol. B25, pp. 451–457, 1969.

C.M. Weeks, et al., "The Crystal Structure of the Copper(II) Complex of L–Isoleucine," Acta Cryst., vol. 25, pp. 443–450, 1969.

B. W. Low, et al., "Glycinate Complexes of Zinc and Cadmium," J. Am. Chem. Soc., vol. 81, pp. 4412–4416, 1959.

D. Van Der Helm, et al., "The Crystal Structure of Bis(L–serinato)zinc," Acta Cryst., vol. 26, pp. 1172–1178, 1970.

A. J. Saraceno, et al., "Infrared Absorption Spectra of Inorganic Coördination Complexes. XVI. Infrared Studies of Glycino–Metal Complexes," J. Am. Chem. Soc., vol. 80, pp. 5018–5021, 1958.

J. V. Dubsky and A. Rabas, "A contribution to the study of the formation of salts with glycine," Spisy vydávané prirodovédeckou Fakultou Masarykovy Univ., No. 123, 3–18, 1930; cf. C.A., vol. 24, 4722.

R. J. Hooper, et al., "Infrared Absorption Spectra of Metal–Amino Acid Complexes. IV. The Infrared Spectra and Configurations of Metal–Isoleucine Chelates," Inorganic Chemistry, vol. 3, No. 11, pp. 1568–1573, 1964.

C. Neuberg, et al., "Heavy–Metal Hydroxides in Statu Nascendi as Reagents for the Purification of Amino Acid Mixtures and the Preparation of Pure Heavy–Metal Salts of Individual Amino Acids," Arch. Biochem., vol. 26, pp. 77–84, 1950.

A. W. Herlinger, et al., "Infrared Spectra of Amino Acids and Their Metal Complexes. II. Geometrical Isomerism in Bis(amino acidato)copper(II) Complexes," J. Am. Chem. Soc., 92:22, p. 6474, 1970.

A. J. Stosick, "The Crystal Structure of Nickel Glycine Dihydrate," J. Am. Chem. Soc., vol. 67, pp. 365–370, Mar. 1945.

T. Sakurai, et al., "Bis(L–histidinato)nickel(II) Monohydrate," Acta Cryst., B34, pp. 660–662, 1978.

P. L. Meredith and R. A. Palmer, "Polarized Crystal Spectra of Bis(DL–histidinato)nickel(II) Monohydrate and Bis(L–histidinato)nickel(II) Monohydrate," Inorganic Chemistry, vol. 10, No. 5, pp. 1049–1056, 1971.

D. Van Der Helm and M. Bilayet Hossain, "The Crystal Structure of Diaquobis(L–serinato)nickel (II)," Acta Cryst., B25, pp. 457–463, 1969.

T. J. Kistenmacher and D. J. Szalda, "Glycylglycinatocopper(II) Dihydrate," Acta Cryst., B31, pp. 1659–1662, 1975.

D. Van Der Helm, et al., "Crystal and Molecular Structure of the Copper(II) Chelate of L–Leucyl–L–tyrosine," Acta Cryst., B31, pp. 1013–1018, 1975.

(List continued on next page.)

Primary Examiner—Porfirio Nazario-Gonzalez

[57] ABSTRACT

Pharmaceutical grade amino acid chelates, free of interfering anions, are made by reacting an amino acid ligand with a metal member selected from the group consisting of elemental metals, metal oxides, metal hydroxides and metal carbonates in an aqueous environment wherein the ligand to metal mole ratio is at least 2:1 and recovering the amino acid chelate from said aqueous environment by means of spray or drum drying. The reaction my be carried out in the presence of non-interfering anions such as anions from citric acid, ascorbic acid, acetic acid, carbonic acid and ammonium and alkali metal salts thereof.

OTHER PUBLICATIONS

W. A. Franks and D. Van Der Helm, "The Crystal and Molecular Structure of the Dimeric Copper(II) Chelate of Glycyl–L–leucyl–L–tyrosine," *Acta Cryst.,* B27, pp. 1299–1320, 1970.

P. De Meester and D. J. Hodgson, "The Crystal and Molecular Structure of Glycyl–L–histidyl–glycinatocopper(II) Dihemihydrate," *Acta Cryst.,* B33, pp. 3505–3510, 1977.

Andreas Rosenberg, "The Infra–Red Absorption Spectra of Some Amide–and Dipeptide–Metal Chelates," *Acta Chemica Scandinavica,* vol. 11, No. 8, pp. 1390–1404, 1957.

R. Strandberg, et al., "The crystal structue of copper(II) monoglycylglycine trihydrate $Cu(NH_2CH_2CONCH_2COO) \cdot 3H_2O$," *Zeitscrift für Kristallographie,* Bd. 116, pp. 266–289, 1961.

A. R. Manyak, et al., "Metal Chelate Compounds of Glycylglycine and Glycylglycylglycine," *Archives of Biochemistry and Biophysics,* vol. 59, pp. 373–382, 1955.

H. C. Freeman and J. T. Szymanski, "Crystallographic Studies of Metal–Peptide Complexes. V. (β–Alanyl–L–histidinato)copper(II) Dihydrate," *Acta Cryst.,* vol. 22, pp. 406–417, 1967.

C. A. Bear and H. C. Freeman, "Crystallographic Studies of Metal–Peptide Complexes. VII. Glycyl–L–methioninatocopper(II)," *Acta Cryst.,* B32, pp. 2534–2536, 1976.

Andreas Rosenberg, "The Infra–Red Absorption Spectra of Some Amino Acid–Metal Chelates at Liquid Air Temperature," *Acta Chemica Scandinavica,* vol. 10, pp. 840–851, 1956.

Kazuo Nakamoto, *Infrared Spectra of Inorganic Coordination Compounds,* 2d ed., Wiley–Interscience, pp. 232–239, 1970.

Howard J. Lucas, Organic Chemistry, Second Ed., American Book Co., New York, pp. 591–594, 1953.

Inomata et al., Bulletin of the Chemical Soc. of Japan, vol. 44, pp. 365–372, 1971.

Chemical Abstracts, vol. 69, Abstract No. 38345, 1967.

Bineev et al., Ozdorovitel'nye Meropriyatiya Prom. Zhivotnovod. Kompleksakh Infekts. Sabol., pp. 71–76, 1983.

Sen et al., Journal of the American Chemical Society, vol. 77, pp. 211–212, Jan. 5, 1955.

Stosick, Journal of the American Chemical Society, vol. 67, pp. 362–365, Mar. 1945.

Kober et al., The Journal of Biological Chemistry, vol. 48, No. 5, pp. 383–411, Nov. 1912.

Advances in Protein Chemistry, edited by Anfinsen et al., vol. 22, Academic Press, NY, pp. 269–270, 391, 1967.

Mathieson et al., Acta Cryst., vol 5, pp. 599–604, 1952.

Van Der Helm et al., Acta Cryst., vol. B25, pp. 451–457, 1969.

Kober et al., The Journal of Biological Chemistry, vol. 13, No. 1, pp. 1–13, 1912.

Weeks et al., Acta Cryst., vol. 25, pp. 443–450, 1969.

Low et al., J. Am. Chem. Soc., vol. 81, pp. 4412–4416, 1959.

Van Der Helm et al., Acta Cryst., vol. 26, pp. 1172–1178, 1970.

Saraceno et al., J. Am. Chem. Soc., vol. 80, pp. 5018–5021, 1958.

Dubsky et al., Chemical Abstracts, vol. 24, Abstract No. 4722, 1931.

Hooper et al., Inorganic Chemistry, vol. 3, No. 11, pp. 1568–1573, 1964.

Neuberg et al., Arch. Biochem., vol. 26, pp. 77–84, 1950.

Herlinger et al., J. Am. Chem. Soc., vol. 92, No. 22, p. 6474, 1970.

Stosick, J. Am. Chem. SOc., vol. 67, pp. 365–370, Mar. 1945.

Sakurai et al., Acta Cryst., vol. B34, pp. 660–662, 1978.

Meredith et al., Inorganic Chemistry, vol. 10, No. 5, pp. 1049–1056, 1971.

Van Der Helm et al., Acta Cryst., vol. B25, pp. 457–463, 1969.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4 and 21 are determined to be patentable as amended.

Claims 2, 5–20 and 22–25, dependent on an amended claim, are determined to be patentable.

New claims 26–44 are added and determined to be patentable.

1. A method for the preparation of pharmaceutical grade amino acid chelates substantially free of interfering anions which comprises reacting an anion free ligand selected from the group consisting of *nonalkaline* naturally occurring amino acids, or dipeptides, tripeptides or quadrapeptides thereof, in an aqueous environment, with a metal metal oxides, metal hydroxides and metal carbonates, wherein the metal is a member selected from the group consisting of calcium, copper, iron, magnesium magnaese and zinc, and wherein the mole ratio of ligand to metal is a least 2:1 and recovering the amino acid chelate thus formed thereform *as a dry powder by bulk drying means*.

3. A method according to claim 2 wherein *the metal member is an elemental metal and* an electrical potential is applied to the aqueous environment to expedite the reaction.

4. A method according to claim 2 wherein *the metal member is an elemental metal and* an electrolyte is added to the aqueous environment to expedite the reaction.

21. A method according to claim 20 wherein said agent is a member selected from the group consisting of carbonic acid [an] *and* ammonium and alkali metal salts thereof.

26. *A method for the preparation of pharmaceutical grade amino acid chelates substantially free of interfering anions which comprises reacting an anion free ligand selected from the group consisting of alkaline naturally occuring amino acids, or dipeptides, tripeptides or quadrapeptides thereof, in an aqueous environment, with a metal member selected from the group consisting of elemental metals, metal oxides, metal hydroxides and metal carbonates, in the presence of an acidic reaction aid selected from the group consisting of a weak organic acid or alkali metal or ammonium salt thereof said weak organic acid being selected from the group consisting of citric acid, ascorbic acid, acetic acid and carbonic acid wherein the metal is a member selected from the group consisting of calcium, copper, iron, magnesium, manganeses and zinc, and wherein the mole ratio or ligand to metal is at least 2:1 and recovering the amino acid chelate thus formed therefrom as a dry powder by bulk drying means.*

27. *A method according to claim 26 wherein the molecular weight of the amino acid chelate formed does not exceed 1500 and wherein the mole ratio of ligand to metal is between about 2:1 and 4:1.*

28. *A method according to claim 27 wherein the metal member is an elemental metal and an electrical potential is applied to the aqueous environment to expedite the reaction.*

29. *A method according to claim 28 wherein the potential is a direct electrical current and wherein the elemental metal forms the anode of an electrolytic cell.*

30. *A method according to claim 26 wherein the metal member is a metal oxide selected from the group consisting of calcium oxide, copper oxide, iron oxide, magnesium oxide, maganese oxide and zinc oxide.*

31. *A method according to claim 30 wherein said aqueous envirnoment consists of sufficient water to bring said metal oxide at least partially into solution.*

32. *A method according to claim 31 wherein said amino acid chelate is recovered from said aqueous environment by means of spray drying or drum drying.*

33. *A method according to claim 26 wherein the metal member is a metal hydroxide selected from the group consisting of calcium hydroxide, copper hydroxide, iron hydroxide, magnesium hydroxide, manganese hydroxide and zinc hydroxide.*

34. *A method according to claim 33 wherein said aqueous environment consists of sufficient water to bring said metal hydroxide at least partially into solution.*

35. *A method according to claim 34 wherein said amino acid chelate is recovered from said aqueous environment by means of spray drying or drum drying.*

36. *A method according to claim 33 whereing said aqueous environment consists of only sufficient water to form a moist past of said metal hydroxide and amino acid chelate ligand.*

37. *A method according to claim 36 wherein said moist past is allowed to stand under ambient conditions for a determind period of time after which it is diluted with water, filtered and the filtrate is spray dried or drum dried.*

38. *A method according to claim 26 wherein the metal member is a metal carbonate selected from the group consisting of calcium carbonate, copper carbonate, iron carbonate, magnesium carbonate, manganese carbonate and zinc carbonate.*

39. *A method according to claim 38 Wherein said aqueous environment consists of sufficient water to bring said metal carbonate at least partially into solution.*

40. *A method according to claim 39 wherein said acidic reaction aid is a member selected from the group consisting of carbonic acid and ammonium and alkali metal salts thereof.*

41. *A method according to claim 40 wherein said metal carbonate is copper carbonate.*

42. *A method according to claim 39 wherein said amino acid chelate is recovered from said aqueous environment by means of spray drying or drum drying.*

43. *A method according to claim 38 wherein said aqueous environment consists of only sufficient water to form a moist paste of said metal carbonate and amino acid chelate ligand.*

44. *A method according to claim 43 wherein said moist paste is allowed to stand under ambient conditions for a determined period of time after which it is diluted with water, filtered and the filtrate is spray dried or drum dried.*

* * * * *